United States Patent [19]

Chee et al.

[11] Patent Number: 5,376,543
[45] Date of Patent: * Dec. 27, 1994

[54] AGROBACTERIUM MEDIATED TRANSFORMATION OF GERMINATING PLANT SEEDS

[75] Inventors: Paula P. Chee, Kalamazoo, Mich.; Stephen L. Goldman, Toledo; Anne C. F. Graves, Bowling Green, both of Ohio; Jerry L. Slightom, Kalamazoo, Mich.

[73] Assignee: The University of Toledo, Toledo, Ohio

[*] Notice: The portion of the term of this patent subsequent to Dec. 8, 2009 has been disclaimed.

[21] Appl. No.: 986,582

[22] Filed: Dec. 7, 1992
(Under 37 CFR 1.47)

Related U.S. Application Data

[63] Continuation of Ser. No. 499,515, Jun. 21, 1990, Pat. No. 5,169,770, which is a continuation of Ser. No. 135,655, Dec. 21, 1987, abandoned.

[51] Int. Cl.⁵ .................... C12N 15/00; C12P 21/04; A01H 1/04
[52] U.S. Cl. ................ 435/172.3; 435/70.1; 435/320.1; 800/DIG. 26
[58] Field of Search ............ 435/69.1, 70.1, 172.3, 435/320.1; 800/205, DIG. 26

[56] References Cited

U.S. PATENT DOCUMENTS 5,169,770  12/1992  Chee et al. .................. 435/172.3

OTHER PUBLICATIONS

Spielmann et al. 1986 Mol. Gen. Genet. 205(1):34–41.
Graves et al. 1986 Plant Mol. Biol. 7:43–50.
Facciotti et al. 1985 Bio/Technology 3:241–246.
Owens et al. 1985 Plant Physiol. 77:87–94.
An et al. 1985 Embo J. 4: 277–284.
Chee et al. 1989 Plant Physiol. 91:1212–1218.

*Primary Examiner*—David T. Fox
*Attorney, Agent, or Firm*—Marshall & Melhorn

[57] ABSTRACT

A non-tissue culture process using Agrobacterium-mediated vectors to produce transgenic plants from seeds of such plants as the common bean and soybean.

3 Claims, 3 Drawing Sheets

AGROBACTERIUM MEDIATED TRANSFORMATION OF GERMINATING PLANT SEEDS

This is a continuation of copending application Ser. No. 07/499,515 filed Jun. 21, 1990, now U.S. Pat. No. 5,169,770, which is a continuation of Ser. No. 07/135,655 filed Dec. 21, 1987, now abandoned.

FIELD OF INVENTION

This invention relates to a process for transforming the germinating seed of a plant and the use of said process to produce transformed plants, particularly dicotyledonous plants.

BACKGROUND OF THE INVENTION

The development of single gene transfer techniques for plant species is of great interest and value to plant breeders because it can be used for the rapid transfer of beneficial genetic traits to plants. Numerous methods have been developed for transferring genes into plant tissues; Agrobacterium-mediated transfer (Murai et al., 1983; Fraley et al., 1983), direct DNA uptake (Paszkowski et al., 1984; Potrykus et al., 1985), microinjection (Crossway et al., 1986), high-velocity microprojectiles (Klein et al., 1987) and electroporation (Fromm et al., 1985; Fromm et al., 1986). A general problem with most of these gene transfer techniques is that the transformed tissues, either leaf pieces or cellular protoplast, must be subjected to some regeneration steps which require a considerable amount of time before a whole plant can be obtained. This process is further complicated because tissue culture procedures have not been established for many crop species. In most cases, gene transfers into crop species have been limited to transformed callus, not whole crop plants. In addition, tissue culture procedures can result in rearrangement of the inserted DNA; or somatic mutations may occur and result in the loss or alteration of desirable genetic traits accumulated by the expertise of many years of plant breeding.

Agrobacterium-mediated gene transfers are by far the most widely used gene transfer techniques, but the use of Agrobacterium strains may be limited because they do not efficiently infect monocotyledonous cereal crop species. However, recent reports (Hooykaas-Van Slogteren et al., 1984; Hernalsteens et al., 1984; Graves and Goldman, 1986; Grimsley et al., 1987; Schafer et al., 1987; Bytebier et al., 1987) suggest that conditions exist whereby Agrobacterium strains can bind to monocotyledonous plant cells and transfer their T-DNA regions into these cells. Interestingly, the report by Graves and Goldman (1986) suggests that Agrobacteria can infect scutellar and mesocotyl cells of germinating corn (Zea mays) seeds and that the resulting plants are transformed, although these transformed plants will be sectored. This technique suggests that Agrobacterium-mediated gene transfer can be accomplished without the need of any tissue culture intermediate steps. Additional support for the transformation of mesocotyl cells of germinating seeds was obtained by Feldmann and Marks (1987) as they were able to obtain G418 resistant Arabidopsis thaliana plants by co-cultivating germinating seeds with Agrobacteria containing a binary plasmid with a plant expressible neomycin phosphotransferase (NPT) II gene in its T-DNA region.

The development of gene transfer techniques for leguminous plants is of commercial interest because it facilitates the development of new cultivars with improved disease resistance, tolerance to specific herbicides and increased nutritional value. Unfortunately, even though these dicotyledonous species are susceptible to Agrobacterium infections (Facciotti et al., 1985; Owens and Cress, 1985; Byrne et al., 1987), its use for transformation is limited due to the lack of available and efficient regeneration procedures, especially for transformed tissues.

Extension of this technique to germinating seed of leguminous plants such as Phaseolus vulgaris, the common bean, is of great importance because regeneration procedures are not available, let alone the regeneration of transformed undifferentiated tissues.

The development of simple, non-tissue culture dependent methods for transfer, stable integration, and sexual transmission of genetic material into plant species is of great interest and importance. Reports from Graves and Goldman (1986) and Feldmann and Marks (1987) present evidence that transformed whole plants can be obtained via Agrobacterium-mediated transformation of the mesocotyl cells of germinating seeds.

The process of this invention represents (1) an improvement of the Graves and Goldman (1986) technique for the transformation of the seeds of monocotyledous plants and (2) its extension to dicotyledonous plants.

INFORMATION DISCLOSURE

An G, Watson et al., (1985) New cloning vehicles for transformation of higher plants. EMBO J. 4:277-284.

Byrne M. C. et al., (1987) Strain and cultivar specificity in the Agrobacterium-soybean interaction. Plant Cell Tissue and Organ Culture 8:3-15.

Bytebier B. et al., (1987) T-DNA organization in tumor cultures and transgenic plants of the monocotyledon Asparagus officinalis. Proc. Natl. Acad. Sci. U.S.A. 84: 5345-5349.

Chee P. P. et al., (1986) Expression of a bean storage protein "phaseolin minigene" in foreign plant tissues. Gene 41:47-57.

Crossway A. et al., (1986) Integration of foreign DNA following microinjection of tobacco mesophyll protoplasts. Mol Gen Genet 202:179-185.

Facciotti D. et al., 1985) Light-inducible expression of chimeric gene in soybean tissue transformed with Agrobacterium Biotechnology 3:241-246.

Feldmann K. A. et al., (1987) Agrobacterium-mediated transformation of germinating seeds of Arabidopsis thaliana: A non-tissue culture approach. Mol Gen Gent 208:1-9.

Fraley R. T. et al., (1983) Expression of bacterial genes in plant cells. Proc Natl Acad Sci U.S.A. 80:4803-4807.

Fromm M. E. et al., (1986) Stable transformation of maize after gene transfer by electroporation. Nature 319:791-793.

Fromm M, et al., (1985) Expression of genes transferred into monocot and dicot plant cells by electroporation. Proc Natl Acad Sci U.S.A. 82:5824-5828.

Graves A. C. F. et al., (1986) The transformation of Zea mays seedlings with Agrobacterium tumefaciens. Plant Mol Biol 7:43-50.

Grimsley N. et al., (1987) Agrobacterium-mediated delivery of infectious maize streak virus into maize plants. Nature 325:177-179.

Hooykaas-Van Slogteren G. M. S. et al., (1984) Expression of Ti plasmid genes in monocotyledonous plants infected with *Agrobacterium tumefaciens.* Nature 311:763-764.

Hernalsteens J. P., et al, (1984) An Agrobacterium-transformed cell culture from the monocot *Asparagus officinalis.* EMBO J 3:3039-3044.

Jefferson (1986) B-Glucuronolose from *Escherichia coli* as a gene fusion marker. Proc. Natl. Acad. Sct., U.S.A. 83:8447-8451.

Klein T. M. et al., (1987). High-velocity microprojectiles for delivering nucleic acids into living cells. Nature 327:70-73.

Murai N. et al., (1983) Phaseolin Gene from Bean is Expressed after transfer to Sunflower via Tumor-inducing Plasmid Vectors. Science 222:476-482.

Owens L. D. et al., (1985) Genotypic variability of soybean response to Agrobacterium strains harboring the Ti or Ri plasmids. Plant Physiol 77:87-94.

Paszkowski J. et al., (1984) Direct gene transfer to plants. EMBO J 3:2717-2722.

Pedersen K. et al., (1986) Sequence analysis ant characterization of a maize gene encoding a high-sulfur zein protein of MW 15,000. J. Biol Ghem 261:6279-6284.

Potrykus I. et al., (1985) Direct gene transfer to cells of a graminaceous monocot. Mol Gen Genet 199:183-188.

Reiss B. et al., (1984). A new sensitive method for qualitative and quantitative assay of neomycin phosphotransferase in crude cell extracts. Gene 30:211-218.

Schafer W. et al., (1987). T-DNA integration and expression in a monocot crop plant after induction of Agrobacterium. Nature 328:539-532.

Slightom J. L. et al,, (1983). Complete nucleotide sequence of a French bean storage protein gene. Phaseolin. Proc Natl Acad Sci U.S.A. 80:1897-1901.

A non-tissue culture approach for preparing transformed *arabidopsis thaliana* seeds is described by Feldmann and Marks,. Mol. Gen. Genet. (1987) 208:19. However, to the inventors' knowledge the application of non-tissue culture transfer has not been successfully applied to leguminous plants and other large seed dicots such as soybean, the common bean, squash, zucchini, peppers, and others.

SUMMARY OF THE INVENTION

Figure 1:
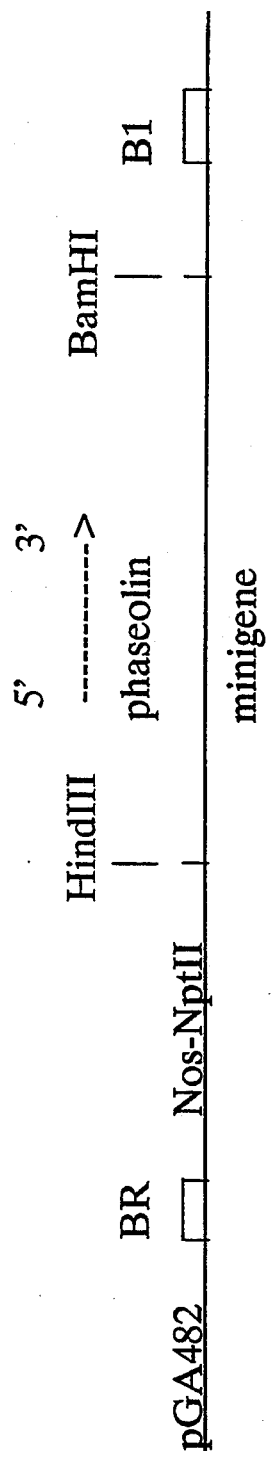
FIG. 1 is a chart showing a physical map of binary plasmids according to the present invention, the map indicating the phaseolin gene.

The present invention provides:

A process for producing a transgenic plant which comprises:

(a) germinating a seed of a plant;

(b) inoculating the meristematic or mesocotyl cells produced during germination, prior to their differentiation, with a virulent or non-virulent Agrobacterium strain containing a transferable gene in an Agrobacterium derived vector; and (c) allowing the cells to differentiate into mature plants, with the proviso that the plant cannot be from the family *Arabidopsis thaliana.*

The time of infecting germinating *P. vulgaris* seed after germination with the Agrobacterium-based vectors has been found to be critical. The length of time the seeds are allowed to germinate prior to Agrobacteria infection will greatly affect the ability of the Agrobacteria to infect meristematic cells, because the amount of vascular tissue is rapidly increasing as differentiation proceeds. However, seed germination must take place in order to have physical access to the mesocotyl region. Therefore a preferred manner of practicing the invention is to conduct the inoculation step within 16 to 96, preferably 24 to 48, hours of germination. To determine the optimum time for infecting germinating seeds, inoculations with virulent Agrobacterium strain A208, were done at various times after initiating germination, between 6 to 96 hours. Successful transformation was scored by gall formation on the developing seedlings, the results of inoculating 50 seeds for each time interval is presented in Table 1. Seeds allowed to germinate between 24 to 48 hours were found to be the most susceptible to Agrobacterium infections. Between 70% to 80% of these inoculated seeds gave rise to seedlings with galls formed either on the hypocotyl, epicotyl, cotyledonary node, or distributed throughout the base of the plant. A preferred method of inoculation is with a virulent or non-virulent Agrobacterium strain containing a transferable DNA cis or trans plasmid.

A particularly preferred manner of practicing the process on dicots involves removing one of the cotyledons prior to inoculation. This step increases access of the strain to the mesocotyl region wherein the meristematic cells are generated.

The method of this invention is simple, rapid, avoids the use of any tissue culture techniques, and transformed plants can be obtained directly.

Also provided are:

Transgenic plants prepared by the process of this invention. Preferred are dicotyledonous transgenic plants. Especially preferred are dicotyldonous plants of the family leguminoseae, such as *phaseolus vulgaris* and *Glycine max.*

DESCRIPTION OF THE PREFERRED EMBODIMENT

Germinating seeds are inoculated with either virulent or non-virulent *Agrobacterium tumefacten* or *Agrobacterium rhizogenes* strains which contain the binary plasmid pGA472 or PGA482 or their derivatives. Both are available from Dr. G. An, Washington State University, Pullman, Wash. This binary plasmid encodes a plant expressible NPT II gene within its T-DNA region and their derivatives contain genes that will convey useful traits to transformed species. Most plants resulting from seeds inoculated with virulent Agrobacterium strains, which also contained the binary plasmid, developed typical crown galls. However, NPT II activity was found in the leaves of some inoculated whole plants, indicating that the binary T-DNA region was also transferred. Transfer of the binary T-DNA region was also accomplished by using avirulent strains of *A. tumefaciens* or rhizogenes. Results presented here show that 1.6% of the *P. vulgaris* and about 1% of the *Glycine max* (soybean) plants were transformed, with transformation being determined by the presence of NPT II enzyme activity.

Seeds of *Phaseolus vulgaris* cv. Olathe or *Glycine max* (cV.A0949) were surface sterilized with 15% Clorox for 10 minutes, followed by 4-5 rinses with distilled water and then placed on moistened paper towels in a temperature controlled Percival incubator at 28° C. and allowed to germinate for various times, 16 to 96 hours. Seed coats were removed and the decoated seeds were opened in halves (that is how cotyledons were removed from the main seed body). The mesocotyl region of the germinating seeds, with their plummule still attached, were infected with an overnight liquid culture of various Agrobacterium strains by using an Eppendorf pipetter fitted with a 27½ gauge needle. Seeds were infected with virulent or avirulent *A. tumefaciens* strains (A208, C58, C58z707 and A208/phas-zein) or *A. rhizogenes* strains [A4RS and A4RS(pR:B278b)pu3.3c-1]. The common *A. tumefaciens* and *A. rhizogenes* strains are available from ATCC, 12301 Parklawn Drive, Rockville, Md. The disarmed *A. rhizogenes* strain RS(pRiB278b) has been described by Vilaine and Casse-Delbart (1987) Mol. Gen. Genet., 206,17 and is available from Dr. F. Casse-Delbart, C.N.R.A., Routede Saint Cyr, F78000, Versailles, France. The disarmed *A. tumefaciens*, strain C582707 is available from Dr. A. G. Hepburn, University of Illinois, Urbana, Ill. Inoculated seeds were then placed on moistened paper towels in petri dishes and incubated at 28° C. After four days these seedlings were transformed to soil and grown to maturity in the greenhouse. Plants infected with virulent strains of *A. tumefaciens* were scored for efficiency of gall formation as a function of germination time.

NPT II Enzyme Activity

NPT II enzyme activity was detected by the in situ gel assay as reported by Reiss et al. (1984). Briefly, 100 mg. of a leaf tissue was mixed with 20 ml. of extraction buffer in a 1.5 ml. Eppendorf tube. Tissue samples were macerated with a Konte pestle and centrifuged for 20 minutes at 4° C. A 35 $\mu$l aliquot of the supernatant solutions was electrophoresed on a non-denaturing 10% polyacrylamide gel. The gel was overlaid with a 1% agarose gel containing 67 mM. tris-maleate (pH 7.1), 42 mM. $MgCl_2$, 400 mM $NH_4Cl$, 20 $\mu$g kanamycin sulfate and 200 $\mu$Ci gamma-[$^{32}$P]ATP. After incubating for 30 minutes at room temperature, the agarose gel was blotted onto Whatman P81 phosphocellulose paper overnight. The P81 paper was removed, washed several times with hot water (80° C.) and autoradiographed.

The following examples utilize many techniques well known and accessible to those skilled in the arts of molecular biology and manipulation of Agrobacterium strains and plasmids (virulent, avirulent, cis- or transconfigurations). Enzymes are obtained from commercial sources and are used according to the vendor's recommendations or other variations known to the art. Reagents, buffers and culture conditions are also known to those in the art. General references containing such standard techniques include the following: R. Wu, ed. (1979) *Meth. Enzymol.* Vol. 68; J. H. Miller (1972) *Experiments in Molecular Genetics;* T. Maniatis et al. (1982) *Molecular Cloning; A Laboratory Manual;* and D. M. Glover, ed. (1985) *DNA Cloning* Vol. II, all of which are incorporated by reference.

The purpose of these examples is to show that gene constructions exist, either constructed by us or others, which when transferred, integrated, and expressed in a plant will convey a useful trait to that plant.

EXAMPLE 1

Figure 2:
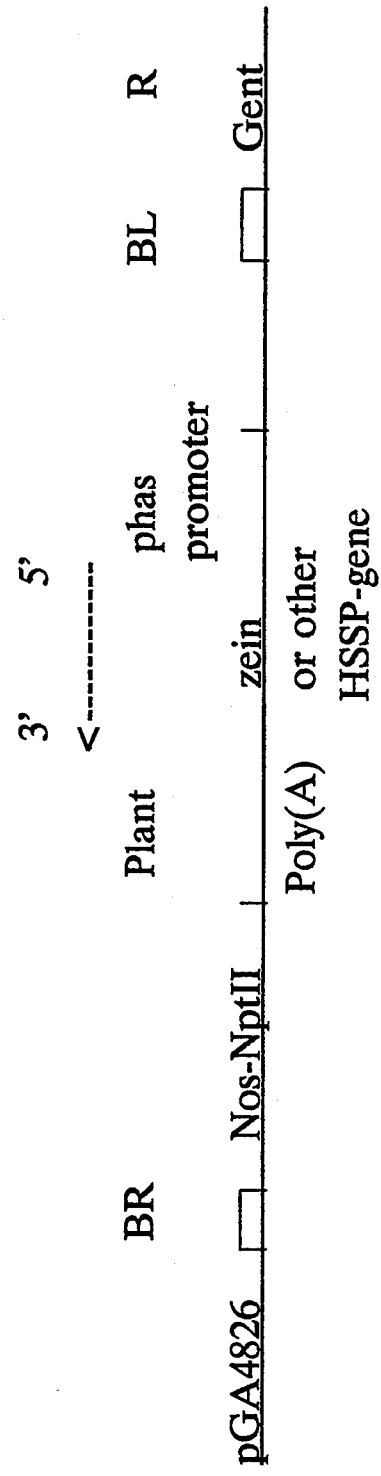
FIGS. 2, 3, 4 and 5 are charts of physical maps of binary plasmids according to the present invention.

Germinating *P. vulgaris* and *G. max* seeds were inoculated about 24 hours after germination with virulent and avirulent Agrobacterium strains which contained modified pGA482G [constructed by clearing the SalF fragment from pWP866 which contains the gene for gentamycin-(3)-N-acetyl-benferose III, and is available from W. Piepersberg, P-8080, Munich, Federal Republic of Germany, into one of the SalI sites in pGA482, based binary vector constructions pPhas-zein [which contains the corn beta-zein gene (Pedersen et al., 1987 and is available from Dr. B. Larkins, Purdue University, West Lafayette, Ind.) transcriptionally linked to the *P. vulgaris* seed storage protein gene promotor (Slightom et al., 1983) or pu3.3c-1 [which contains the phaseolin minigene construction (Chee et al., 1985) and is available from Agrigenetics Corp, Madison, Wis.]. Physical maps of these binary plasmids are presented in FIG. 2.

Transfer and expression of the plant expressible NPT II gene contained within the T-DNA region of pGA482G (An et al., 1984) was determined by removing two to three young leaves (usually obtained 10 inches or more above the wound site resulting from inoculating the germinating seeds), extracting the soluble proteins and testing for NPT II activity. From a total of 695 plants tested only 11 plants showed NPT II activity in these protein extracts. They are listed in Table II and the NPT II positive results are shown in Table II. About 1.6% of the surviving inoculated seeds show NPT II activity, suggesting that the T-DNA region of the binary plasmid pGA482G is integrated in the genome of these *P. vulgaris* plants.

Other procedures, well known to those skilled in the art, such as microinjection and high-velocity microprojectiles, can be used to transfer DNAs into the mesocotyl region and that transformed plants should result.

TABLE I

| Frequency of Gall Formation on Seedlings Inoculated With the Agrobacterium Strain A208 ||
|---|---|
| Germination Periods | Frequency of Gall Formation |
| 6 hours | 0 |
| 12 hours | 0 |
| 24 hours | 80 |
| 36 hours | 70 |
| 48 hours | 40 |
| 72 hours | 10 |
| 90 hours | 10 |

TABLE II

| NPT II Positive Transformed Plants | | |
|---|---|---|
| Plant Number | Binary Construction | Gall |
| 40 | C58/phas-zein | + |
| 41 | C58/phas-zein | + |
| 46 | C58/phas-zein | + |
| 61 | C58/phas-zein | − |
| 65 | C58/phas-zein | − |
| 151 | C58/phas-zein | + |
| 258 | A4RS(pR:B278b)pu3.3c-1 | − |
| 269 | A4RS(pR:B278b)pu3.3c-1 | − |
| 296 | A4RS(PR:B278b)pu3.3c-1 | − |
| 470 | A208/phas-zein | − |
| 552 | C58Z707/phas-zein | − |

EXAMPLE 2

Construction of a micro-Ti plasmid for the expression of a phaseolin mini-gene. The transfer and expression of this gene will increase the level of seed storage protein in the transformed plant.

2.1

Using the *P. vulgaris* seed storage protein gene, phaseolin, and its cDNA counterpart a mutant phaseolin gene lacking its five introns was constructed. This mutant phaseolin gene (phas-minigene) retains it natural 5' and 3' plant-regulatory sequences and the construction of this plasmid (pPv3.3-cDNA) has been described by Chee et al. (1986) *Gene* 41:47 and Cramer et al. (1985) *Proc. Natl. Acad. Sci.* 82;334 and is available from Agrigenetics Corp. Madison, Wis. Plasmid pPv3.3-cDNA was subjected to restriction enzyme digests, BamHI and HindIII and a 3.6 kb fragment was removed and cloned into BglII and HindIII sites of the binary vector pGA482 (An et al. (1985) *EMBO. J.* 4:277). This construction places this mutant phaseolin gone within the right and left borders of the binary plasmid, now referred to as pµ3.3c-1, and along side of the plant expressible NPT II gene which is used for selection and identification of transformed plants. The structure of binary plasmid pu3.3c-1 is shown in FIG. 1.

2.2 Use of pu3.3c-1

This binary plasmid has to be transferred into various Agrobacterium strains, i.e. A208, C58, C58:707, LBA4404 and A4RS, etc. The method described here can be used to transfer the binary plasmid pµ3.3c-1 into various plant species (e.g., common bean, soybean and other large seeded plants). In addition, multiple copies of the phaseolin minigene can be placed into the binary plasmid by subcloning the NcoI to BamHI fragment (3 kb fragment) from pFv3.3-CDNA into NcoInd BamHI digested clone pPr 8.8 g (available from J. Slightom, The Upjohn Company, Kalamazoo, Mich.) which replaces the genomic part with the CDNA region of pPV3.3-cDNA. This cloning experiment results in obtaining subclone pFv8.3-cDNA which contains an upstream BglII site (Slightom, et al. (1983) *Proc. Natl. Acad. Sci.*, 80:1897) which allows for the isolation of a BglII-BamHI 3.3,5 kb fragment which was recloned into the BamHI digested plasmid pPv3.3-cDNA. The orientation of the new phaseolin insert(s) can be checked and only those in the 5' and 3' orientation with respect to the first phaseolin gone are used for additional insertions. Because only the 3' BamHI site was retained (the BglII/BamHI lighted site is not digestible by either enzyme) this step could be repeated any number of times, depending on plasmid stability and ability to still transform *E. coli* and Agrobacteria. This procedure was repeated to obtain as many as four phaseolin gene inserts, which were cloned using a HindIII and BamHI digest into the binary plasmid pGA482G. Having a series of these plasmids with different numbers of phaseolin genes (this can also be referred to as gene family transfer since a family of similar genes is transferred in a single event) will increase the level of storage proteins in seeds of transformed plants.

EXAMPLE 3

The purpose of this example is to incorporate a modified seed storage protein which encodes a higher percentage of sulfur-containing amino acids; such a gene is referred to as High Sulfur Storage Protein (HSSP)-gene. This gene is constructed so that it is developmentally expressed in the seeds of dicotyledonous plants; this has been accomplished by using the phaseolin promoter. The modified gene must encode a substantial number of sulfur-containing amino acids. Naturally occurring HSSP-genes can also be used. The two best naturally occurring HSSP-genes are the beta zein gene (15 kD) (Pedersen et al (1986) *J. Biol. Chem.* 201:6279) and the Brazil nut protein (Altenbach et al. (1987) *Plant Mol. Bio.* 8:239). However, any other natural or synthetic gene derivative of an HSSP-gene can be used for the improvement of the nutritional value of seeds.

3.1 Construction of a HSSP-gene

The construction of the zein derivative HSSP-gene uses the phaseolin gene promoter from clone pPv8.8-Bg [constructed by doing sight specific modification of pPv8.8g. The BglII to XbaI fragment for pPV8.8g was cloned into M13mp 17 (commercially available) to obtain clone as 13mp18PV1.6. This was then used to produce single-stranded DNA which was annealed to an oligomer (30 residues) which contained a two-base pair change from the original phaseolin promoter region. The sequence of the oligomer was 5'CATCATAG-TAGATCTAGTATTGAATATGAG-3' (opposite to coding strain). After annealing DNA polymerase I (Klenow fragment) was added and the remaining opposite strand of M13MP18pv1.6 was synthesized. The mutant M13 clone, containing a new Bgl site 7 bp from the translation start site (Slightom et al, 1983, ibid) of the phaseloin gene, was screened using the 32p-labeled oligomer and differential temperature hybridization. Cloned candidates were further analyzed by doing Bgl II digestions and agarose gel electrophoresis to identify particular clones containing the extra Bgl II site, the appearance of the Bgl II to Bgl II 800 bp fragment. The modified clone m13 mp181.6 30.12.3 was isolated and DNA was isolated. From the isolated DNA an NcoI to XbaI fragment was removed and cloned into NcoI and the partial XbaI digested p 8.8g. The new clone containing the phaseolin promoter on a 800 bp Bgl II to Bgl II fragment was designated p PvS.8.8g Bg.] to ensure proper expression and at a level expected for a seed storage protein, and the beta-zein clone pZG15RX (Pedersen et al., ibid). The phaseolin promoter was made accessible by a site specific mutation at position −7 which resulted in a BglII site, thus the phaseolin promoter could be removed after a BglII digest as an 800 bp fragment. This fragment was subcloned into the BamHI site of pUC18 (available from commercial sources), yielding a plasmid designate pUC-Pvpro. The beta-zein structural gene, including signal peptide, coding region, and Poly (A) addition signal was removed from plasmid pZG15EX (available from B. Larkins, Purdue University, West Lafayette, Ind.) after a TaqI digestion and this fragment was cloned into the AccI site of pUC-Pvpro, yielding clone pUC-Phas-zein. This Phas-zein gene was removed by digestion with HindIII and EcoRI and this fragment was cloned into the binary vector pGA482G, which had previously been digested with HindIII and EcoRI. This new binary plasmid is referred to as pGA482G-Phas-zein (see FIG. 2) and it was transferred into Agrobacterium strains: A208, C58, LBA4404. C58Z707 and A4RS which in turn can be used to produce transformed plants in accordance with the method of this invention.

A phase zein construction similar to that described above has been transferred into dicotyledonous plants and its developmental expression in the seeds of the transformed plant has been observed; see Hoffman et al. (1987) *EMBO J.* 6:3213. Additional modification has been made to a Phas-zein gene construction. These modifications include the ligation of a BglII linker onto its 5'-end and a BamHI linker onto its 3'-end which allows the construction of multiple copies of the phase zein gene as described above for the phaseolin minigene. This allows for the transfer of a HSSP-gene multigene family into a plant species by a single transformation event and the expression of higher levels of the HSSP-gene product. This leads to the development of dicotyledonous plant varieties which are nutritionally improved, such as common bean, soybean and other large seeded plants.

EXAMPLE 4

Transfer of Viral Resistance

The purpose of this example is to generate a construction for the expression of a plant virus coat protein gene which, when expressed in a dicotyledonous plant, results in reduced symptoms or resistance to later infections by that virus (see report by Powell-Abel et al. (1986) *Science* 232:738). Viral coat proteins are isolated from any number of plant virus classes (tobamo, cucumo, poty, tobra, AMV, etc.) and they are expressed constitutively in plants after the attachment of the CaMV 35S promoter. In addition, a plant poly (A) signal is added to the 3' region to ensure proper expression.

Figure 3:
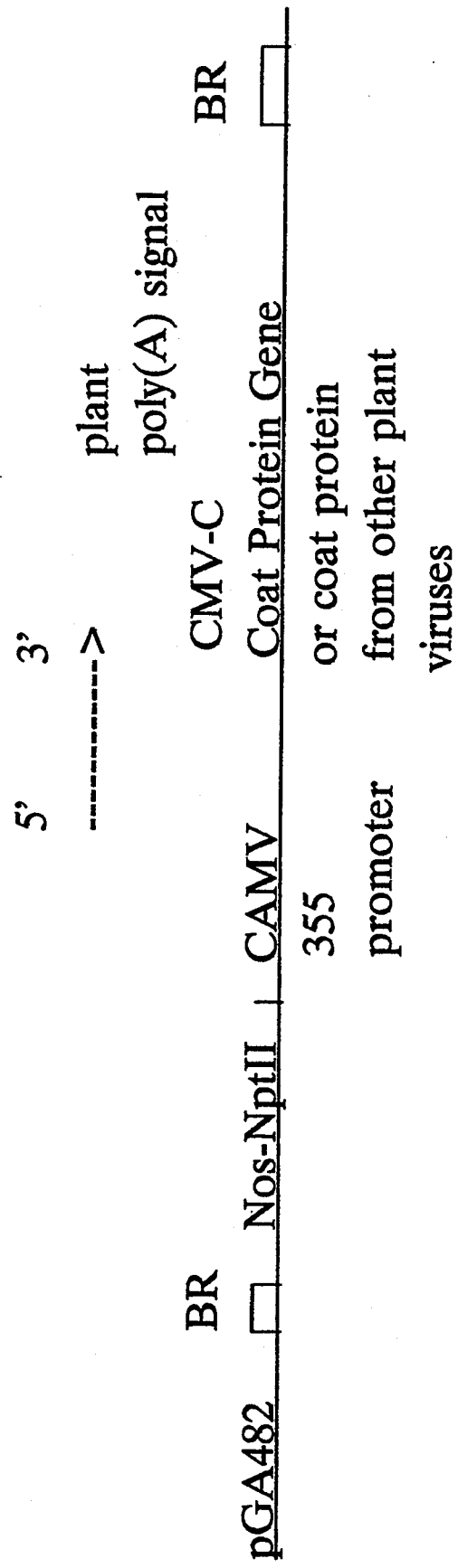

A clone containing any specific viral coat protein gene can be obtained for both plant DNA and RNA viruses. Such is the case for cucumber mosaic virus strain C (CMV-C); its RNA genome was copied into double-stranded cDNA and the coat protein gene was isolated and characterized as follows. A residues were added to the 3' end of CMV-C total RaH, using *E. coli* polyadenylose. This poly (A) region was used to anneal an aligo dT primer which was used to prime the synthesis of single-stranded (SS) cDNA using reverse transriptos and appropriate buffer of CMV-C SS-cDNA, double-stranded cDNA was synthesized by adding RNaso H to remove the RNA from the duplex and the second strand was made by adding *E. coli* DNP polymerase I (Klenow fragment) and the appropriate buffer. After synthesis of CMA-C ds-DNA, it was *E. coli* methylated using Eco RI methylase and Eco methylent buffer, thus protecting all internal Eco RI sites in the CMV-C ds-cDNA molecules. After eco methylation the CMV-C ds-cDNA molecules were treated again with *E coli* polymorse I (Klenow fragment) to ensure that all ends (5' and 3') were flush, then these molecules were ligated to Eco RI linkers using T4-Ligase. After ligation the CMV-C ds-cDNA molecules were separated from contaminating linker by size fractionation on a GYOG column (1 cm×30 cm). The fraction containing the majority of the CMV-C ds-cDNA molecules was EtOH precipitated, followed by resuspension in 10 µg of H2O. About 100 µg of these Eco RI linked CMV-C ds-cDNA molecules were removed and mixed with 1 µg of λ gT11 arms (commercially available) and ligated together using T4 ligase. The recombinant GT 11-CMV-C were plated using *E coli* Up50supF as host and these plates ($10^{-4}$ clones) were screened for clones containing CMV-C coat protein gene coding region using p-labeled CMV-whiteleaf SS-cDNA as probe. From this screening, a clone, λ GT11-CMV9.9 was isolated. It contained an EcoRI insert of 1400 base pair, enough to encode the complete CMV coat protein. This CMV coat protein gene can be expressed in plant tissues once a plant-active promoter and poly (A) signal are attached to its 5' and 3' regions, respectively. The scheme to accomplish this is shown in FIG. 3.

Attachment of the constitutive cauliflower mosaic virus (CaMV) 35S promoter was done by first doing a partial AccI and complete EcoRI digests of clone pCMV9.9 which was obtained by cloning the Eco RI insert from Lambda GT11-CMV9.9 into EcoRI cut puc 19 (commercially available ). The 1100 bp CMV- C coat protein gene fragment was removed, both ends were blunted, and this fragment was cloned into the SmaI site of pDH51 (Pietrzak et al. (1986). *Nuc. Acids Res.* 14:5857) which is available from A. T. Mohn, Friedrick Mieschen Institut, Basel, Switzerland to obtain clone pDH51/cP19. This positioned the CMV-C coat protein gene downstream of the CaMV 35S promoter and upstream from the CaMV poly (A) signal sequence. To ensure a high level of expression other poly (A) signal sequences (which may function better than the CaMV 35S poly (A) signal) can be attached, such as the poly (A) signal from the seed storage protein gene phaseolin (Slightom et al. (1983) *Proc. Natl. Acad. Sci.* 80:1897). To facilitate engineering, this plant expressible CMV-C coat protein gene was removed from clone pDH51/CP19 by an EcoRI digest and the 1800 bp fragment was cloned into pUC1813 (which contains more restriction enzyme sites and is available from Dr. R. Kay, Washington State University, Pullman, Wash. The resulting clone, pUC1813/CP19, was then partially digested with HindIII and the 1800 bp fragment was cloned into the binary vector pGA482 to obtain the new clone, pGA482/CP19H (see FIG. 3). This binary plasmid, or its derivatives, can be transferred into Agrobacterium strains: A208, C58, LBA4404, C58Z707, A4RS, A4RS(pRiB28b) and others. Using the transformation method of this invention, this plant expressible CMV-C coat protein gene (or any other plant virus coat protein gene) can be transferred into a dicotyledonous plant species such as, cucumber, squash, melon, zucchini, pepper, etc. The development of these new cultivars are useful because of their resistance to infections by specific virus or viruses (if more than one virus coat protein gene construction is transferred to a single plant).

EXAMPLE 5

Transfer of Herbicide Resistance

The purpose of this example is to illustrate how to generate plant expressible genes which allow a plant to be resistant to specific classes of herbicides. Such plants are useful for many reasons; (i) herbicides normally lethal can be used, and (ii) different crops can be used in close rotations on soil which may contain residual amounts of a previously used herbicide that is normally lethal to the second crop. Two genes of interest are mutant derivatives (derived from plant or bacterial sources) of the acetolactate synthase (ALS) gene which are not sensitive to chlorsulfuron and sulfometuron methyl herbicides (Falco et al., (1985) *Biotech. Plant Sci.* Academic Press, Inc. page 313) and mutants of the gene encoding enolpyruvylshikimate-3-phosphate synthase (EPSPS) (Stalker et al, (1985) *J. Biol. Chem.*, 260:4724) which are not sensitive to the herbicide glyphosate.

Figure 4:
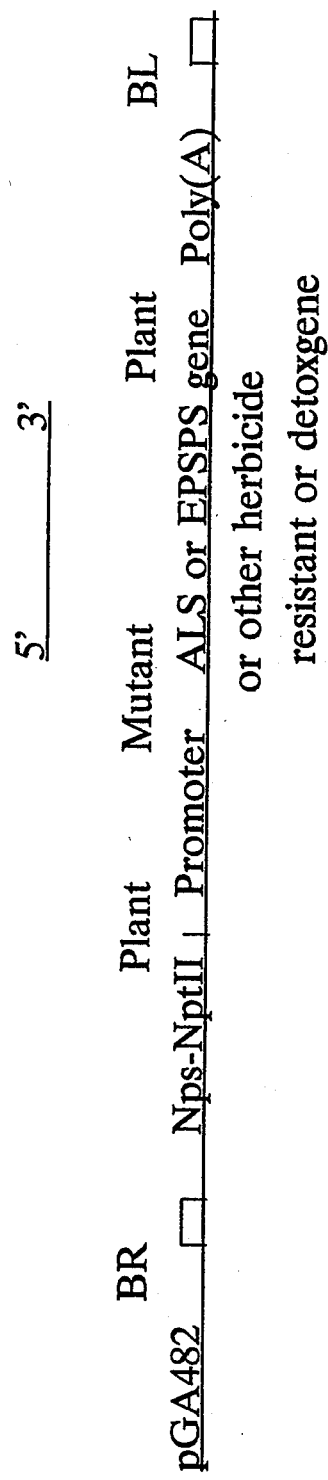

A gene which encodes an important enzyme which is either resistant to or detoxifies a specific herbicide is cloned downstream from a plant active promoter, such as: CaMV 35S, ribulose-1,5-bisphosphate carboxylase small subunit gene, or other strong plant gene promoter and upstream from a plant gene poly (A) signal sequence, see FIG. 4.

This gene is then be cloned into an Agrobacterium-derived vector (either binary or cis) and using the above-described plant transformation method, such a gene is be transferred into many dicotyledonous plant species, such as: soybean, common bean, peppers, melons, etc.

EXAMPLE 6

Transfer of Insect-Resistant Gene

Figure 5:
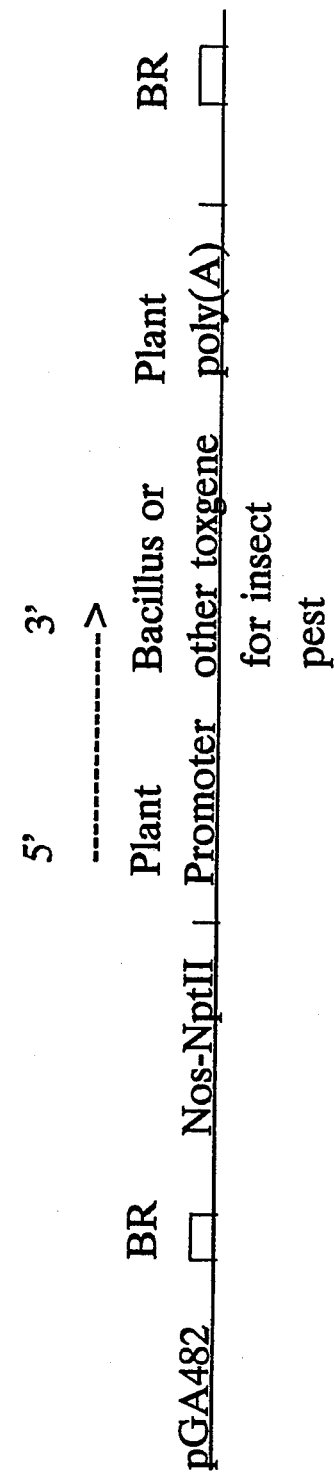

In nature, numerous polypeptides exist which are toxic to insect pests. The best known protein toxins are those associated with different strains of *Bacillus thuringiensis;* for example, *B. israelenis* active against Diptera (mosquitoes and blackflies), *B. thuringinensis* active against Lepidoptera, and *B. san diego* active against Coleoptera. The toxic protein found in each of these bacteria is highly specific to insect pests; they are not toxic to other organisms. Thus the transfer and expression of genes encoding such toxic proteins in plants are beneficial in reducing insect damage without using chemical insecticides thereby avoiding risk to other organisms. The genes encoding many of these toxic proteins have been isolated and sequenced (Schnepf et al. (1985) *J. Biol. Chem.,* 260:6264; Waalwijk et al., (1985) *Nucl. Acids Res.,* 13:8207; Sekar et al (1987) *Proc. Natl. Acad. Sci.,* 84:7036). The transfer of the *B. thuringiensis* toxic gene into tobacco and its usefulness in protecting the plant from insect damage has been reported (Vaeck et al. (1987) *Nature* 328:33). Thus, the combination of using the plant transformation system described here and plant expressible Bacillus toxin gene (see FIG. 5) allows for the transfer of a useful trait to any dicotyledonous species for which tissue-culture based transformation systems are inefficient or have not been developed, such as: common bean, soybean, melon, cucumber, squash, zucchini, pepper, etc.

We claim:

1. A non-tissue culture process for producing a transgenic soybean plant, which process comprises:
    (a) germinating a seed of a *Glycine max* plant for about 24 to 48 hours;
    (b) inoculating the meristematic or mesocotyl cells produced by the germinating seed of step (a), prior to differentiation of said cells, with an armed or disarmed Agrobacterium strain containing an Agrobacterium-derived vector, said vector containing a transferable gene; and
    (c) allowing the cells to differentiate into a mature plant.

2. A process according to claim 1, wherein the vector is a plasmid adapted for transfer in either trans or cis configuration.

3. A process according to claim 1, wherein the vector is a binary vector comprising a plasmid adapted for transfer in the trans configuration.

* * * * *